(12) United States Patent
Yuz (10) Patent No.: US 11,508,485 B2
(45) Date of Patent: Nov. 22, 2022

(54) AUTOMATED RISK OF DISEASE CALCULATION SYSTEM FOR MOBILE DEVICES

(71) Applicant: USARAD HOLDINGS, INC., Fort Lauderdale, FL (US)

(72) Inventor: Michael Yuz, Oakland Park, FL (US)

(73) Assignee: USARAD HOLDINGS, INC., Fort Lauderdale, FL (US)

( * ) Notice: Subject to any disclaimer, the term of this patent is extended or adjusted under 35 U.S.C. 154(b) by 102 days.

(21) Appl. No.: 17/007,913

(22) Filed: Aug. 31, 2020

(65) Prior Publication Data
US 2022/0068487 A1 Mar. 3, 2022

(51) Int. Cl.
*G16H 50/30* (2018.01)
*G16H 10/20* (2018.01)
*G06Q 20/32* (2012.01)

(52) U.S. Cl.
CPC ........... *G16H 50/30* (2018.01); *G06Q 20/325* (2013.01); *G16H 10/20* (2018.01)

(58) Field of Classification Search
CPC ....... G16H 50/30; G16H 10/20; G06Q 20/325
USPC .......................................... 705/2–3
See application file for complete search history.

(56) References Cited

U.S. PATENT DOCUMENTS

| | | | |
|---|---|---|---|
| 2008/0275729 A1 | 11/2008 | Taggart | |
| 2009/0177405 A1 * | 7/2009 | Niggebrugge | G16H 50/30 702/19 |
| 2010/0234691 A1 | 9/2010 | Iwano | |
| 2011/0093295 A1 * | 4/2011 | Mankad | G16H 10/60 705/500 |
| 2012/0090043 A1 | 4/2012 | Twizere | |
| 2017/0262604 A1 * | 9/2017 | Francois | G16H 10/60 |
| 2020/0135326 A1 * | 4/2020 | Averbach | G16H 40/20 |

OTHER PUBLICATIONS

National Heart, Lung, and Blood Institute, Assessing Your Weight and Health Risk, Mar. 14, 2006, https://www.nhlbi.nih.gov/health/educational/lose_wt/risk.htm (Year: 2006).*

(Continued)

*Primary Examiner* — Joy Chng
(74) *Attorney, Agent, or Firm* — Burr & Forman LLP; Jeffrey H. Kamenetsky (57) ABSTRACT

A computer-implemented method including receiving, at a processing device of a disease risk calculation server, a request from a user mobile device for a disease risk calculation and including an answer, determining at the processing device, diseases the user is likely to contract, providing, from the processing device, the determined diseases, receiving, at the processing device, a user selection of a disease that user is likely to contract, providing, from the processing device, a question related to a proven risk factor of the user selected disease, receiving, at the processing device, a user answer, calculating, at the processing device, a risk that the user will contract the selected disease, providing, from the processing device, the calculated risk to the mobile device, and receiving and processing electronic payment from the user device after receipt by the user mobile device of the calculated risk, the electronic payment being governed by blockchain technology.

20 Claims, 11 Drawing Sheets

(56) References Cited

OTHER PUBLICATIONS

Cancer.Net, Understanding Cancer Risk, Mar. 2018, https://www.cancer.net/navigating-cancer-care/prevention-and-healthy-living/understanding-cancer-risk (Year: 2018).*

International Search Report and Written Opinion dated Jan. 10, 2022, International Searching Authority, International Application No. PCT/US21/48249.

* cited by examiner

AUTOMATED RISK OF DISEASE CALCULATION SYSTEM FOR MOBILE DEVICES

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A SEQUENCE LISTING, TABLE OR COMPUTER PROGRAM LISTING APPENDIX

Not Applicable

BACKGROUND OF THE INVENTION

1. Field of the Invention

The present disclosure relates generally to systems and methods for assessing the risk of a person contracting a disease. In particular, examples of the present disclosure are related to an automated risk of disease calculation system for mobile devices.

2. State of the Prior Art

Personalized medicine is a medical model that provides a customized approach to patient healthcare by taking into account information particular to a patient in determining medical decisions, practices and products. While patient healthcare has always been personal to the patient, personalized medicine, leveraging advances in digital technologies, human genetics, and molecular biology, provides a level of personalization not previously achievable by traditional medicine. For example, genetic testing for disease-causing mutations in certain genes can inform patients as to whether they are at higher risk for cancer and suggest individualized prophylactic therapies.

Integral to personalized medicine is the identification of a patient's immediate and long-term health risks to establish goals and actions to decrease risks and improve health. Identification of the patient's health risks takes into account all available patient information such as the patient's demographic information, family history, medical history, genetic testing, and relevant laboratory test results.

Proven risk factors associated with thousands of diseases are known. In addition, increasing numbers of genetic diseases caused by abnormalities in genes and chromosomes are becoming known. Although this information is available to specialized medical personnel, it is not conveniently available to users on an accessible platform.

BRIEF SUMMARY OF INVENTION

Examples of the present disclosure are directed to apparatus and methods that are described in the following Brief Description of the Drawing Figures and Detailed Description of the Invention. Non-limiting and non-exhaustive embodiments of the present disclosure are described in the following detailed description of the invention made with reference to the following figures, wherein like reference numerals refer to like parts throughout the various views unless otherwise specified.

Skilled artisans will appreciate that elements in the figures are illustrated for simplicity and clarity and have not necessarily been drawn to scale. For example, the dimensions of some of the elements in the figures may be exaggerated relative to other elements to help improve the understanding of various embodiments of the present disclosure. Also, common but well-known elements that are useful or necessary in a commercially feasible embodiment are often not depicted in order to facilitate a less obstructed view of these various embodiments of the present disclosure.

DETAILED DESCRIPTION OF THE INVENTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example", or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

In accordance with various embodiments of the present disclosure, techniques are described for providing an automated risk of disease risk calculation system for mobile devices. Furthermore techniques are described that enable a user of a mobile device to determine, using his mobile device, his risk of contracting any of a plurality of diseases. Techniques are also described that enable a user of a mobile device to receive, on his mobile device, suggestions for reducing his risk of contracting a disease he is determined to be at risk of contracting. Additionally techniques are described that it possible for a user of a mobile device to receive, on his mobile device, a second opinion from an expert regarding his risk of contracting a disease he is determined to be at risk of contracting.

Figure 1A:
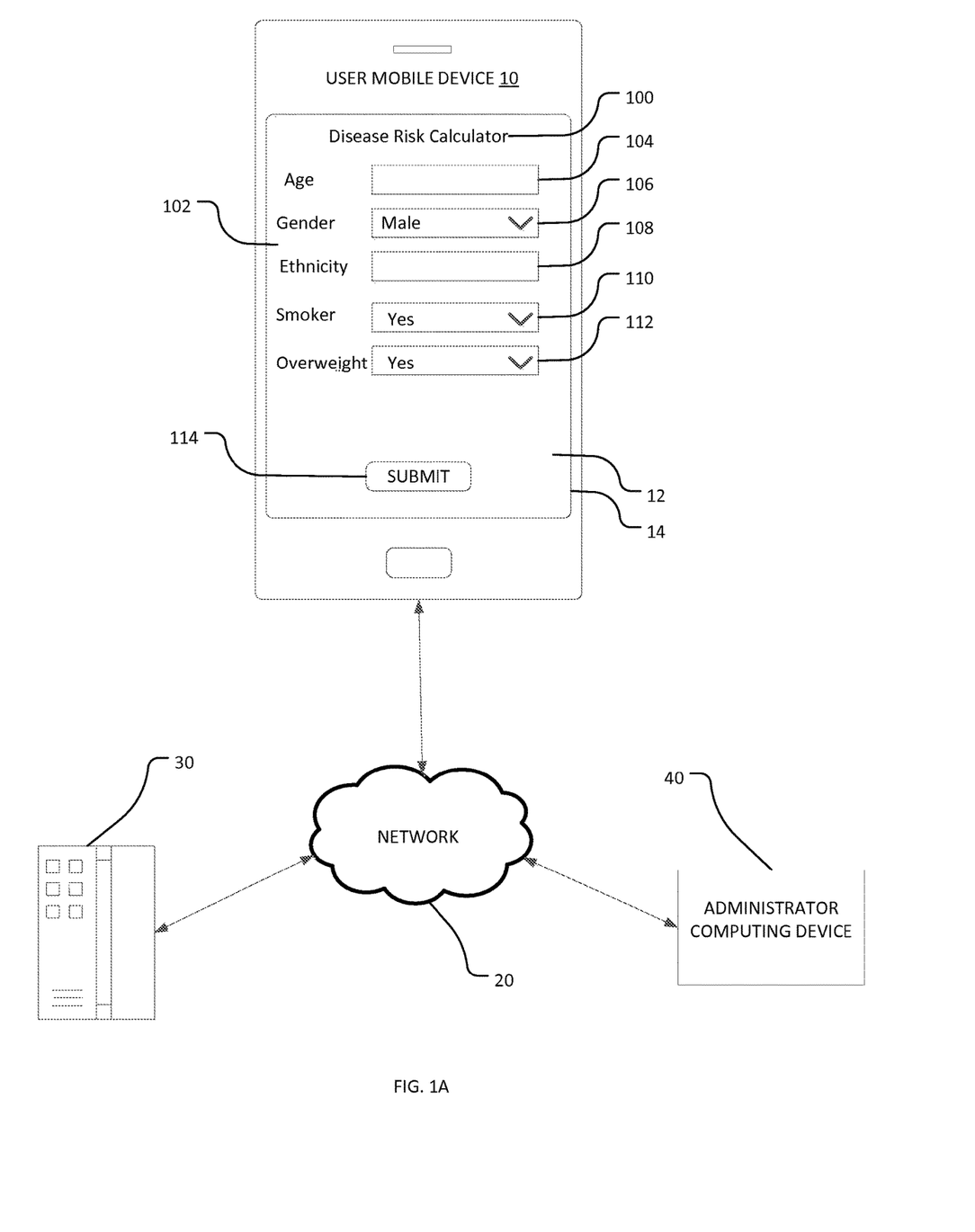
FIGS. 1A-1H are schematics illustrating a user's mobile device displaying a graphical user interface in communication with a disease risk calculation server in accordance with some embodiments of the present disclosure.

Referring now to FIG. 1A, a user mobile device 10 in communication with a disease risk calculation server 30 and an administrator computing device 40 via a network 20 is illustrated. The user mobile device 10 can include any of a plurality of handheld computing devices manufactured by companies including, but not limited to, Apple, Nokia, HTC, Blackberry and Motorola Mobility that have an operating system (such as the iPhone OS and Android operating system) capable of running a plurality of types of application software known as apps. In the illustrated example, the user mobile device 10 is displaying a graphical user interface (GUI) 12 on a touch screen 14 of the user mobile device 10. While a touch screen 14 is illustrated, it should be appreciated that other user interfaces can be used to allow the mobile device user to interact with his mobile device 10. For example, in some embodiments of the present disclosure the user interface may employ voice recognition techniques to accept user input. While one disease risk calculation server 30 is illustrated, the term "disease risk calculation server" refers to one or more servers that operate in an individual or distributed manner. The administrator computing device 40 can include a mobile computing device such as a mobile telephone, laptop computer, and tablet computer, or a stationary computing device such as a desktop computer. Further, as used herein, the term "network" can refer to any communication network including, but not limited to, a wireless network, a cellular network, an intranet, the Internet, or combinations thereof.

In one embodiment of the present disclosure, the GUI 12 of the user mobile device 10 allows the user to submit a request for a disease risk calculation to the disease risk calculation server 30. From a downloadable disease risk calculation app running on the user mobile device 10 and represented by the icon 100, the GUI 12 can display a plurality of selectable fields 102 in which the user can enter demographic and other information including a field 104 in which the user can enter his age, a field 106 in which the user can select his gender, a field 108 in which the user can enter his ethnicity, a field 110 in which a user can select whether he is a smoker, and a field 112 in which the user can select whether or not he is overweight. In some embodiments of the present disclosure, the selectable fields 102 allow the user to enter specific health conditions such as diabetes, hypertension, skin issues, heart issues, back pain after surgery, medications being taken, and family history of cancer. In other embodiments of the present disclosure, the selectable fields 102 allow the user to enter the results of lab tests, including genetic testing for disease-causing mutations. In yet other embodiments of the present disclosure, the selectable fields 102 allow the user to select an application running on the user's mobile device 10 capable of collecting and electronically transmitting accurate diagnostic information such as the user's weight, blood pressure, laboratory test results and electrocardiograms. The GUI 12 can further display a button 114 that indicates that the user is requesting a disease risk calculation.

When the user has entered his answers in selectable fields 102, he can press, or otherwise select, the button 114 to request a disease risk calculation. When the user presses the button 114, the user mobile device 10 can transmit the user's request to the disease risk calculation server 30 via the network 20. The request can include the user's answers and selections entered in the selectable fields 102.

The disease risk calculation server 30 can receive the request from the user's mobile device 10 and can perform a request analysis to determine a set of diseases that the user is likely to contract. By way of example and not limitation, if the user indicates that he is male, diseases that only females contract are excluded from the set of diseases that the user is likely to contract. Further, if the user indicates that he is aged, he is more likely to contract diseases such as cancer, osteoarthritis, cardiovascular disease, dementia, Alzheimer's disease, and diabetes. If the user indicates that he is aged and has cardiovascular disease or diabetes, then the set of diseases that the user is likely to contract may include stroke and heart attack. The request analysis performed by the disease risk calculation server 30 preferably takes into account as many of the answers and selections entered by the user in the selectable fields 102. The request analysis further preferably determines the set of diseases that the user is likely to contract based on the degree of association between the users entered answers and selections and the risk of contracting particular diseases.

Figure 1B:
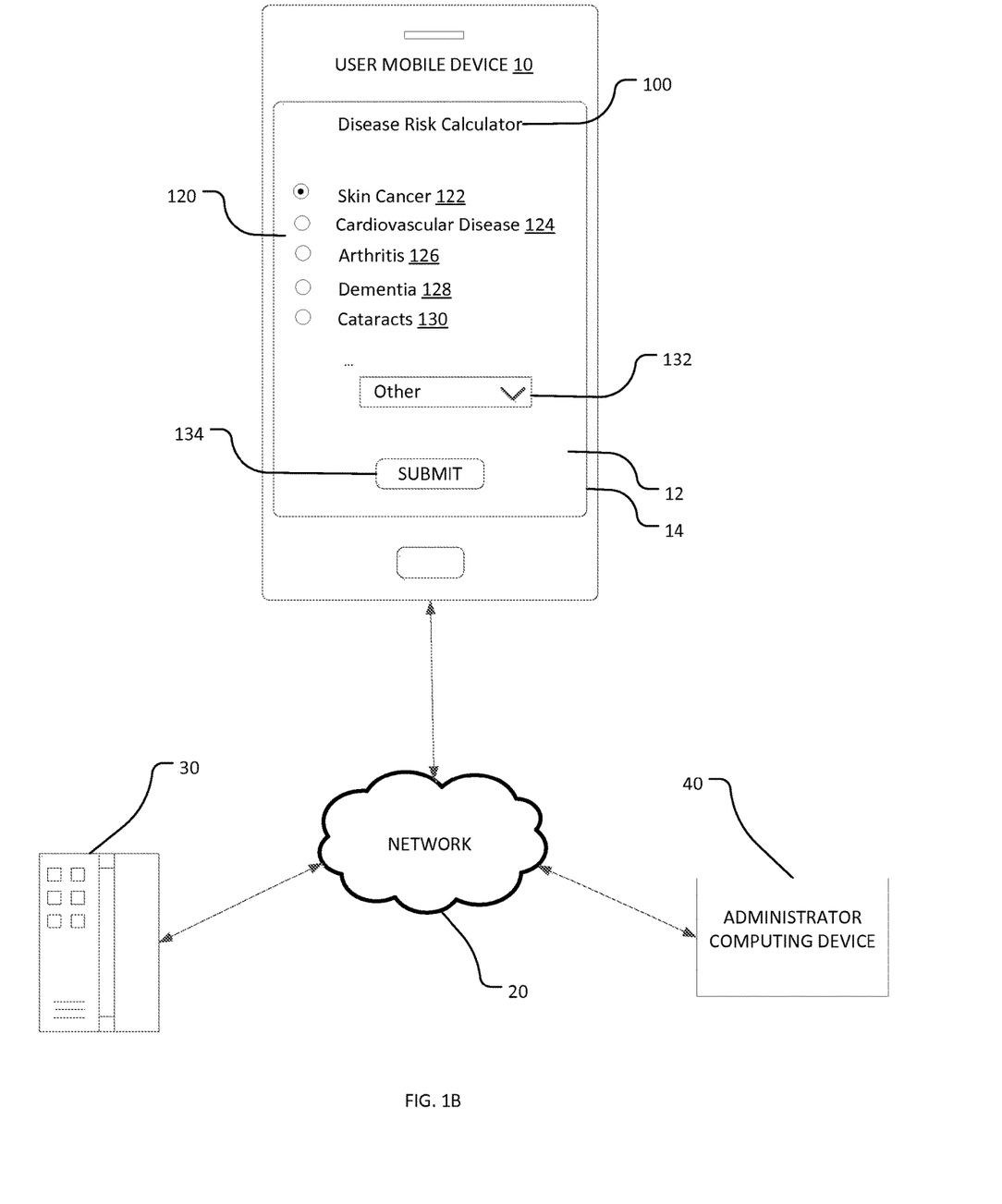

The disease risk calculation server 30 can then transmit the determined set of diseases that the user is likely to contract to the user's mobile device 10. Upon receiving the set of diseases that the user is likely to contract from the disease risk calculation server 30, the user's mobile device 10 can display the set in the GUI 12, thereby allowing the user to select a disease from the set and request a calculation of his risk of contracting the selected disease from the disease risk calculation server 30. FIG. 1B illustrates an example of the user's mobile device 10 displaying a set of diseases 120. The set of diseases 120 is illustrated as including skin cancer 122, cardiovascular disease 124, arthritis 126, dementia 128, and cataracts 130. In addition, the GUI 12 can display a drop-down menu 132 that provides the user with a list of selectable diseases that can include any disease for which known risk factors are available. By this means, the user can request a determination of his risk of contracting any disease for which there are proven risk factors. The GUI 12 can further display a button 134 that provides the user with a means of submitting his selected disease to the disease risk calculation server 30.

Figure 1C:
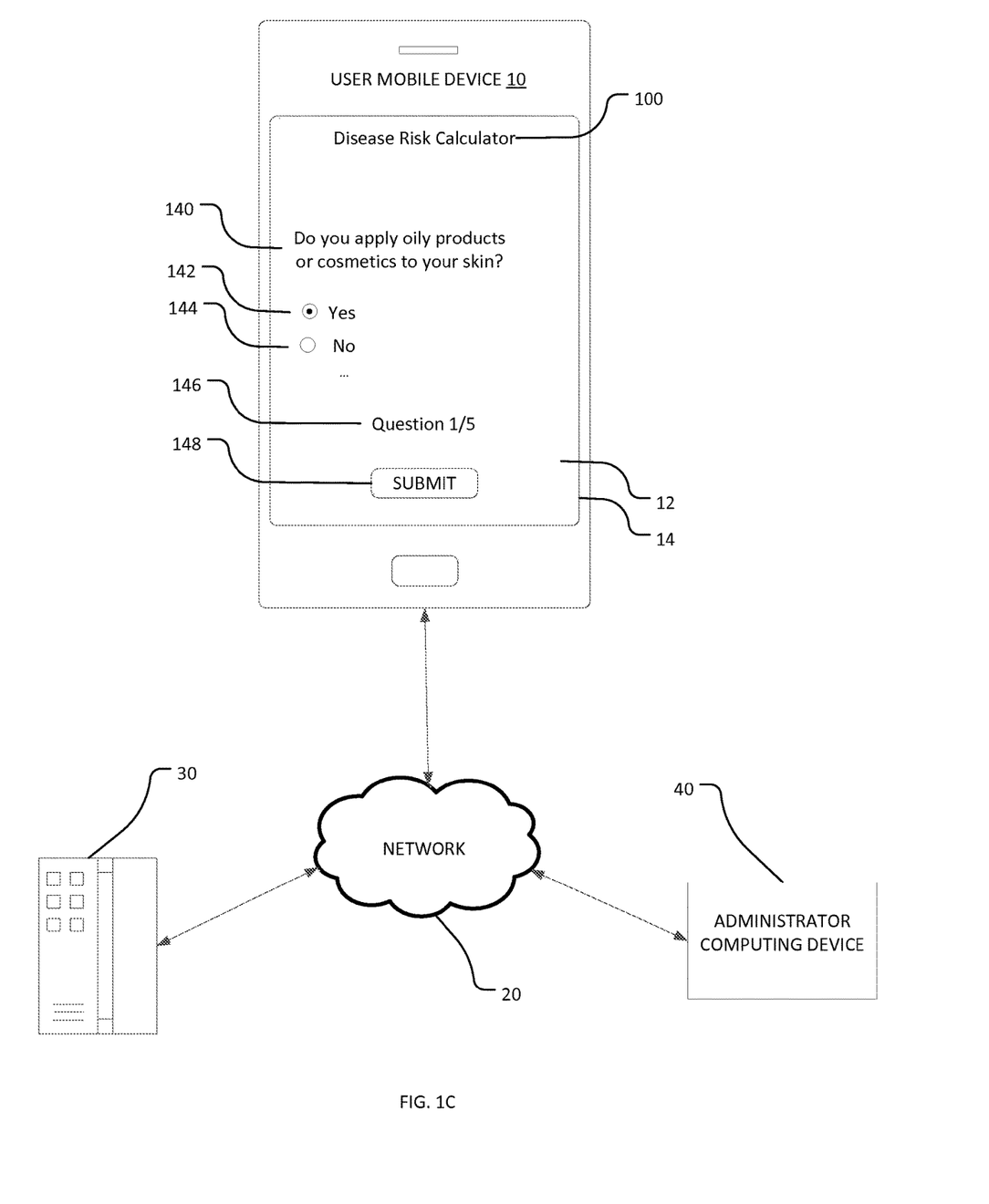

The disease risk calculation server 30 can receive the user's selection and transmit at least one question to the user's mobile device 10. The at least one question can represent a proven risk factor. A risk factor is proven if the evidence is strong enough to show a link or association between the disease and the risk factor. FIG. 1C illustrates an example of the user's mobile device 10 displaying a first question 140. The GUI 12 can display buttons 142 and 144 that provide the user with the option of answering the question 140 in the affirmative (button 142) or in the negative (button 144). In some embodiments of the disclosure, the user can be given other options in answering the question 140. For example, the user can be given the option of answering the question 140 with either "Frequently", "Seldom", or "Never". In some embodiments of the disclosure, an indication 146 of the number of questions to be served to the user is given. In other embodiments of the disclosure, the user is given the option of returning to the previous GUI 12 shown in FIG. 1B by means of a "BACK" button (not shown). The GUI 12 can further display a button 148 that allows the user to submit his response to the question 140 to the disease risk calculation server 30.

An administrator computing device 40 provides a system administrator with the ability to manage a database of associations between each of a plurality of disease and proven risk factors as well as the questions transmitted to the user's mobile device 10. Given the complexity of the information available to health care professionals, including increasingly affordable and available genetic information and proven disease risk factors discovered by researchers on an almost daily basis, the administrator computing device 40 allows system administrators update the database and to add, delete and edit questions provided to the user of the mobile device 10 to thereby maintain the accuracy of the calculated disease risk.

Figure 1D:
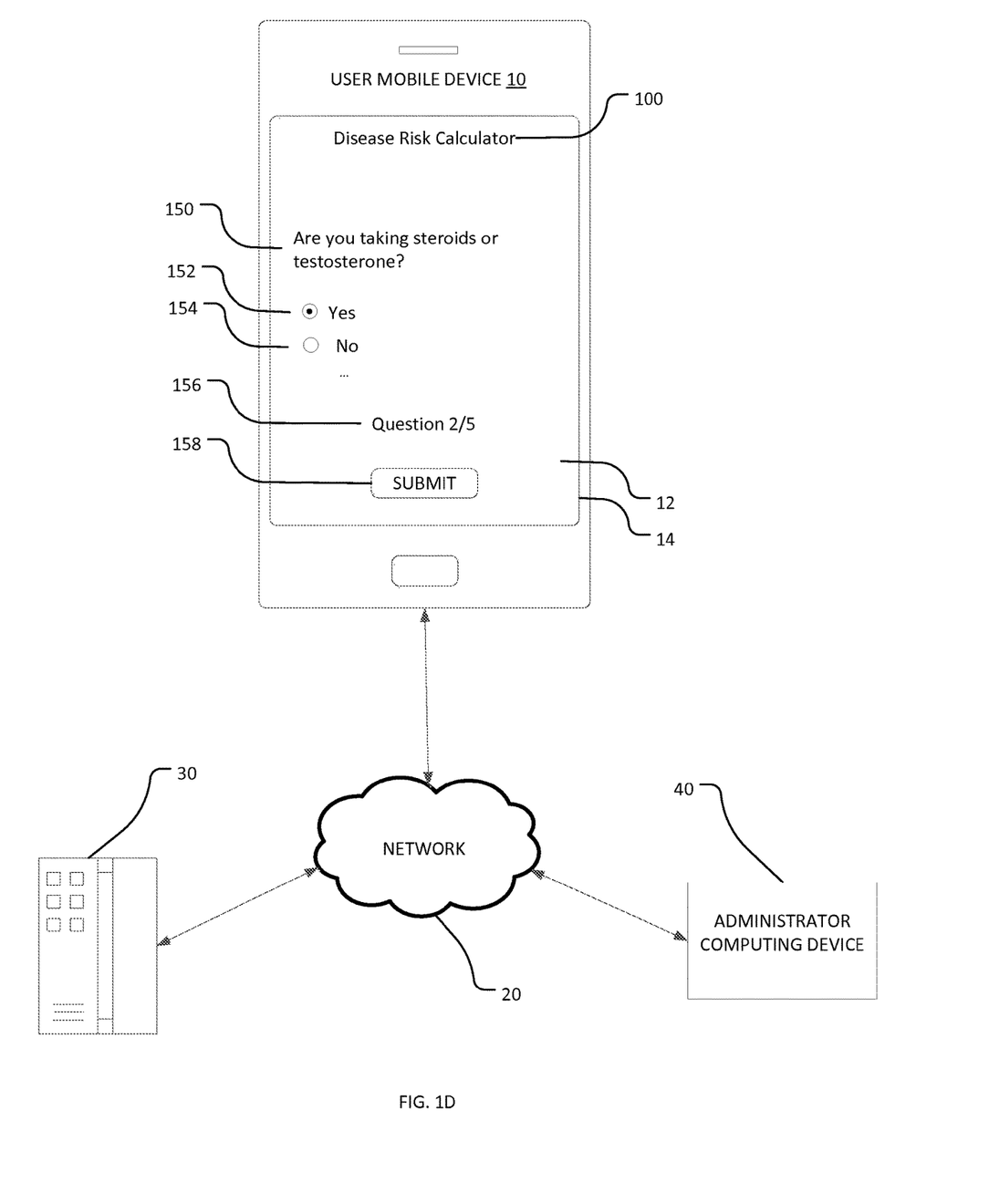

The disease risk calculation server 30 can receive the user's selected answer to the question 140 and transmit another question to the user's mobile device 10. FIG. 1 D illustrates an example of the GUI 12 displaying a second question 150. The GUI 12 can display buttons 152 and 154 that provide the user with the option of answering the question 150 in the affirmative (button 152) or in the negative (button 154). In some embodiments of the disclosure, the user can be given other options in answering the question 140. For example, the user can be given the option of answering the question 140 with either "Frequently", "Seldom", or "Never". In some embodiments of the disclosure, an indication 156 of the number of questions to be served to the user is given. In other embodiments of the disclosure, the user is given the option of returning to the previous GUI 12 shown in FIG. 1C by means of a "BACK" button (not shown). The GUI 12 can further display a button 158 that allows the user to submit his response to the question 150 to the disease risk calculation server 30.

The disease risk calculation server 30 can receive the user's answer to the question 150 and transmit additional questions to the user's mobile device 10. In the illustrated example, the disease risk calculation server 30 can transmit three additional questions to the user's mobile device 10 and receive the user's answers thereto. Exemplary questions include "Do you sweat a lot?", "Do you live in a humid climate or are you exposed to significant humidity?", and "Do or did either of your parents have a similar problem?".

Using the user's answers to the submitted questions, the disease risk calculation server 30 can calculate a risk that the user will contract the selected disease. In some embodiments of the present disclosure, the disease risk calculation server 30 is operable to calculate the risk by assigning equal weights to each of the risk factors and assigning a high risk if, using the example illustrated in FIGS. 1A-1D, the user indicates that he has four or five of the five risk factors, a moderate risk if the user indicates that he has two or three of the five risk factors, and a low risk if the user indicates that he has none or one of the five risk factors. In other embodiments of the present disclosure, the disease risk calculation server 30 is operable to calculate the risk by assigning weights corresponding to the degree of association between each risk factor and the disease. For example, a risk factor indicating a disease-causing mutation may be assigned a greater weight than and environmental or lifestyle risk factor. In yet other embodiments of the present disclosure, the disease risk calculation server 30 is operable to calculate the risk using known algorithms developed for each of a plurality of diseases.

In some embodiments of the present disclosure, the disease risk calculation server 30 can calculate the risk that the user will contract the selected disease as a percentage. In other embodiments of the present disclosure, the disease risk calculation sever 30 can calculate the risk that the user will contract the selected disease within a given time period. For example, the risk that the user will contract the selected disease can be calculated to be 50% within 5 years or 70% within 10 years.

Figure 1E:
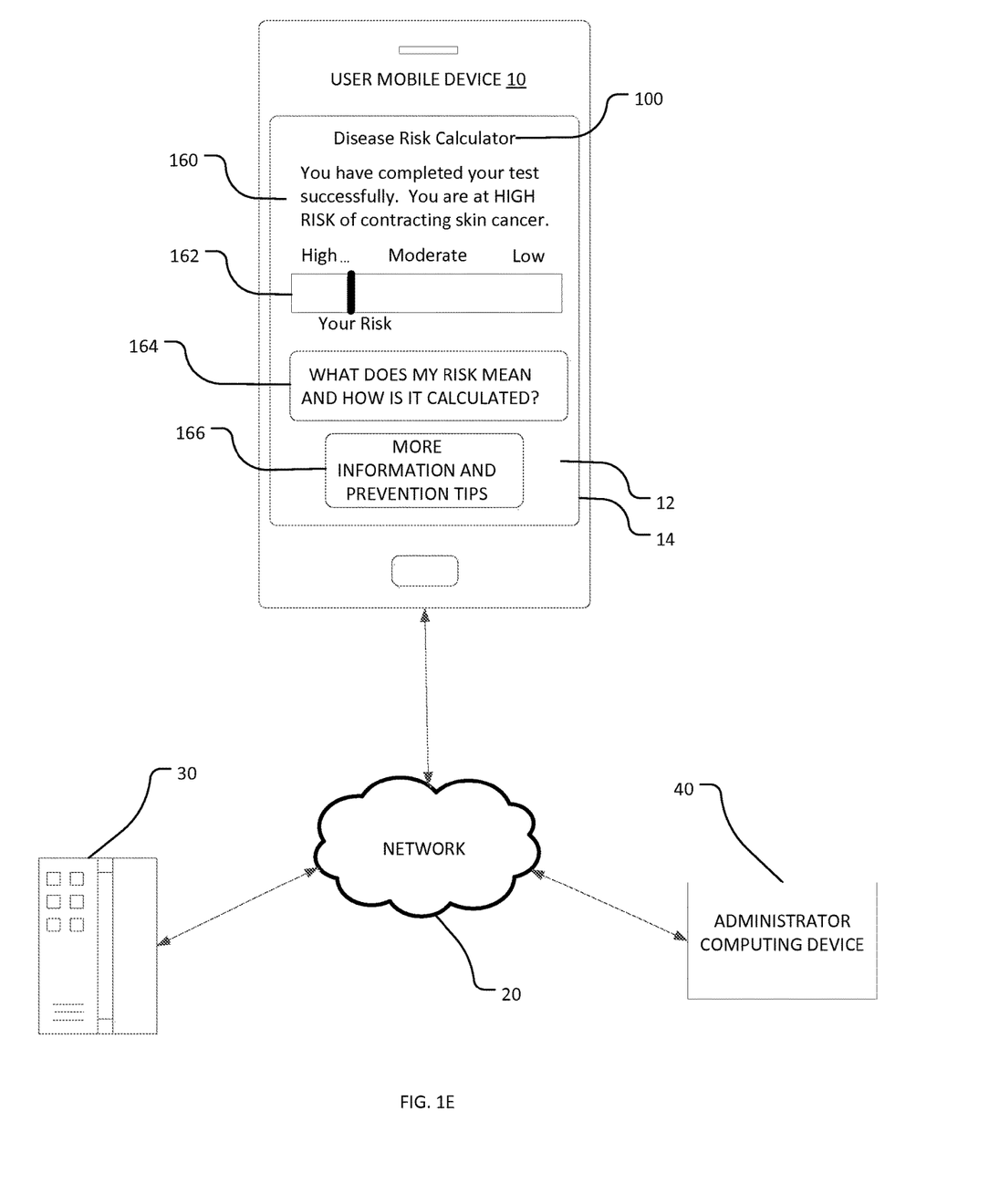

The disease risk calculation server 30 can transmit the calculated risk to the user's mobile device 10. FIG. 1 E illustrates an example of the user's mobile device 10 displaying a calculated risk of the user contracting skin cancer. The GUI 12 can display a text message 160 as well as a graphical display 162 indicating the user's calculated risk. In some embodiments of the present disclosure, the risk can be displayed as a percentage. In other embodiments of the present disclosure, the risk can be displayed as a percentage over a time period. The GUI 12 can also display a button 164 that when selected by the user provides the user with an explanation of the calculated risk and of how the risk was calculated. The GUI can further display a button 166 that when selected by the user provides the user with additional information regarding the disease and prevention tips.

Figure 1F:
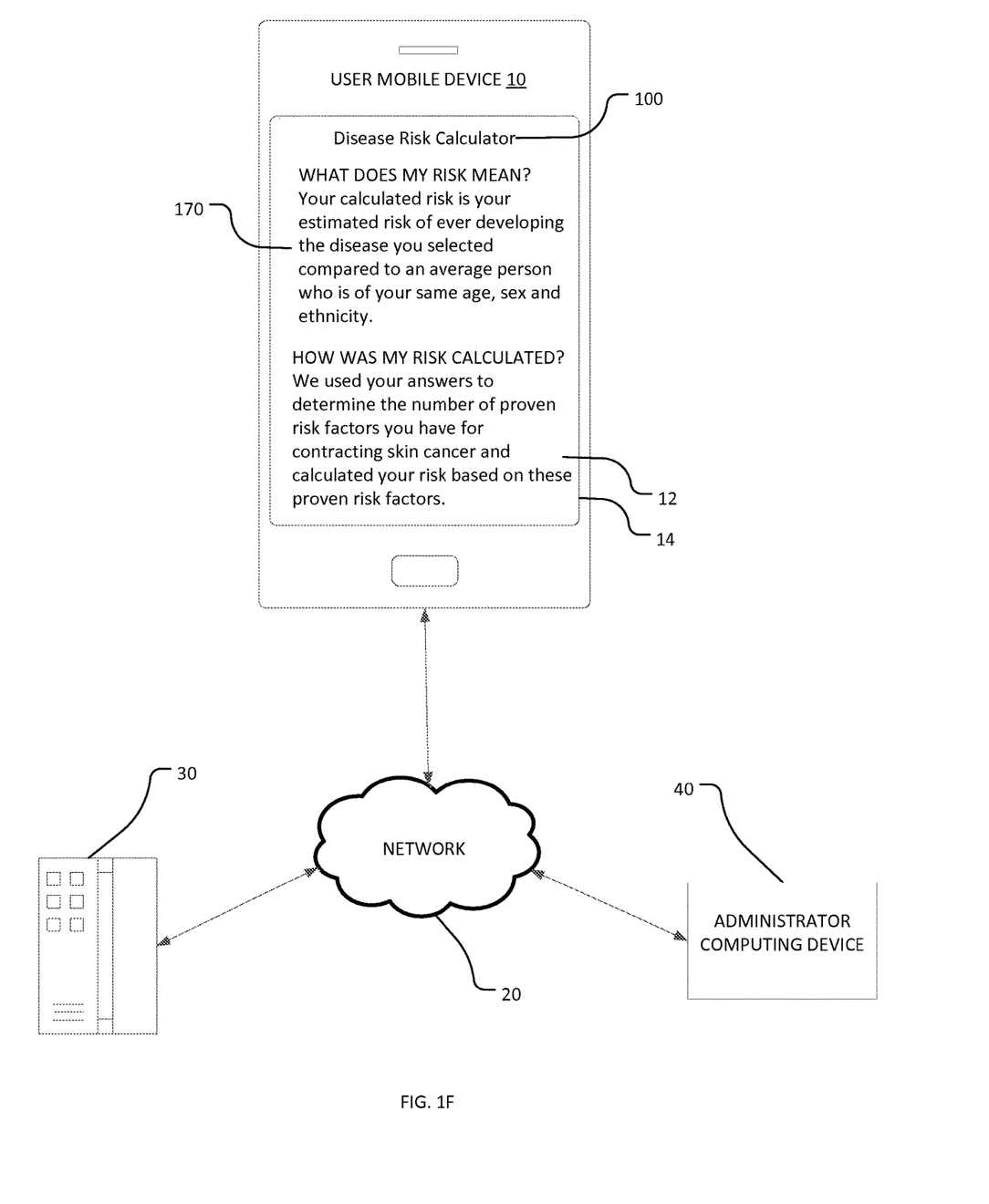

The disease risk calculation server 30 can receive the user's selection of the button 164 indicating that the user wants an explanation of what the risk means and how the risk was calculated. The disease risk calculation server 30 can transmit an explanation to the user's mobile device 10. FIG. 1F illustrates an example of the user's mobile device 10 displaying the provided explanation of what the risk means and how the risk was calculated. The GUI 12 can display the explanations in a text message 170.

Figure 1G:
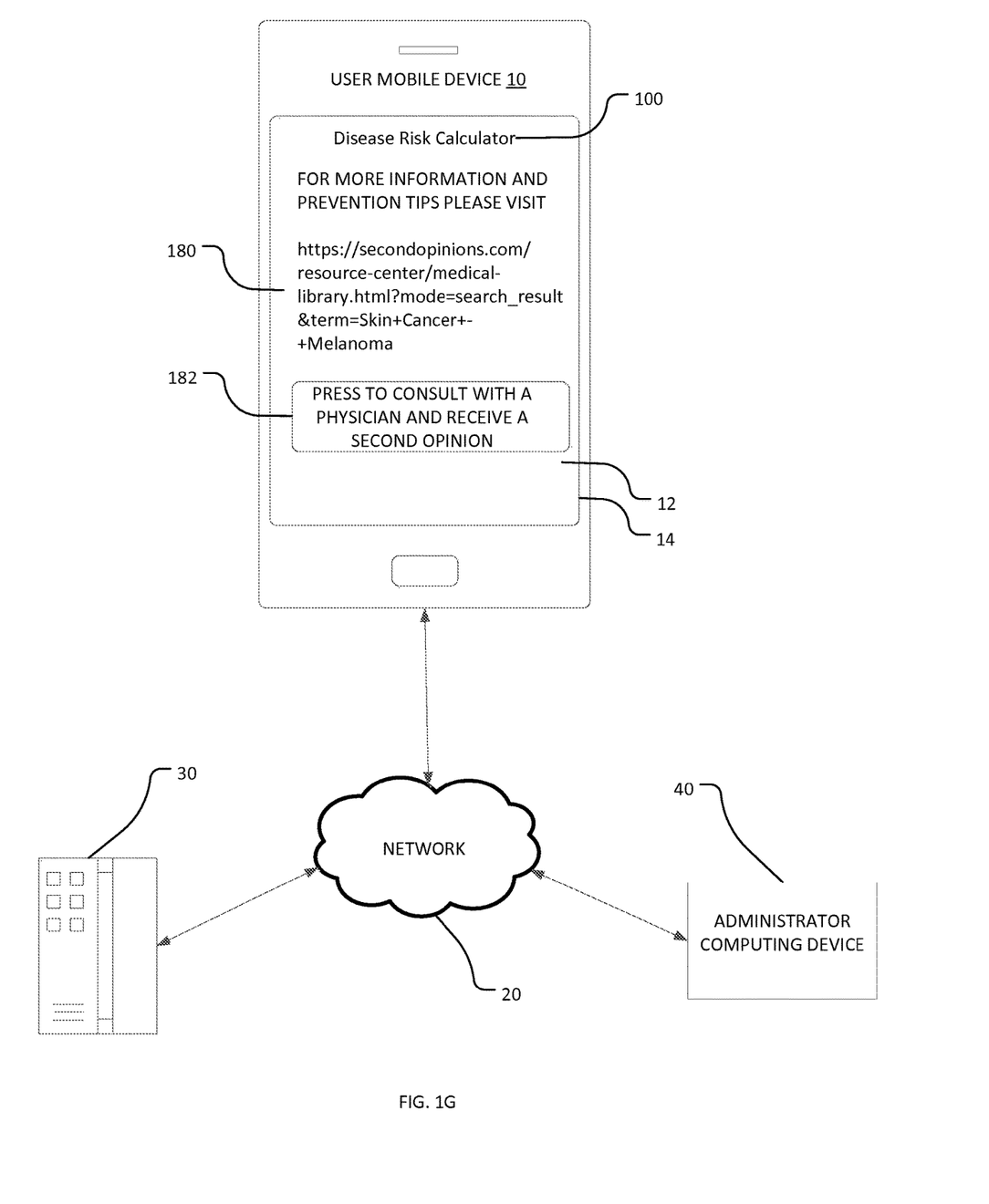

The disease risk calculation server 30 can receive the user's selection of the button 166 indicating that the user wants additional information and prevention tips. The disease risk calculation server 30 can transmit to the user's mobile device 10 a link to a website where the additional information and prevention tips related to the user's selected disease are made available. FIG. 1G illustrates an example of the user's mobile device 10 displaying the provided link. The GUI 12 can display the provided link 180. The GUI 12 can further display a button 182 that provides the user with the option of consulting with a physician and receiving a second opinion regarding the calculated risk.

Figure 1H:
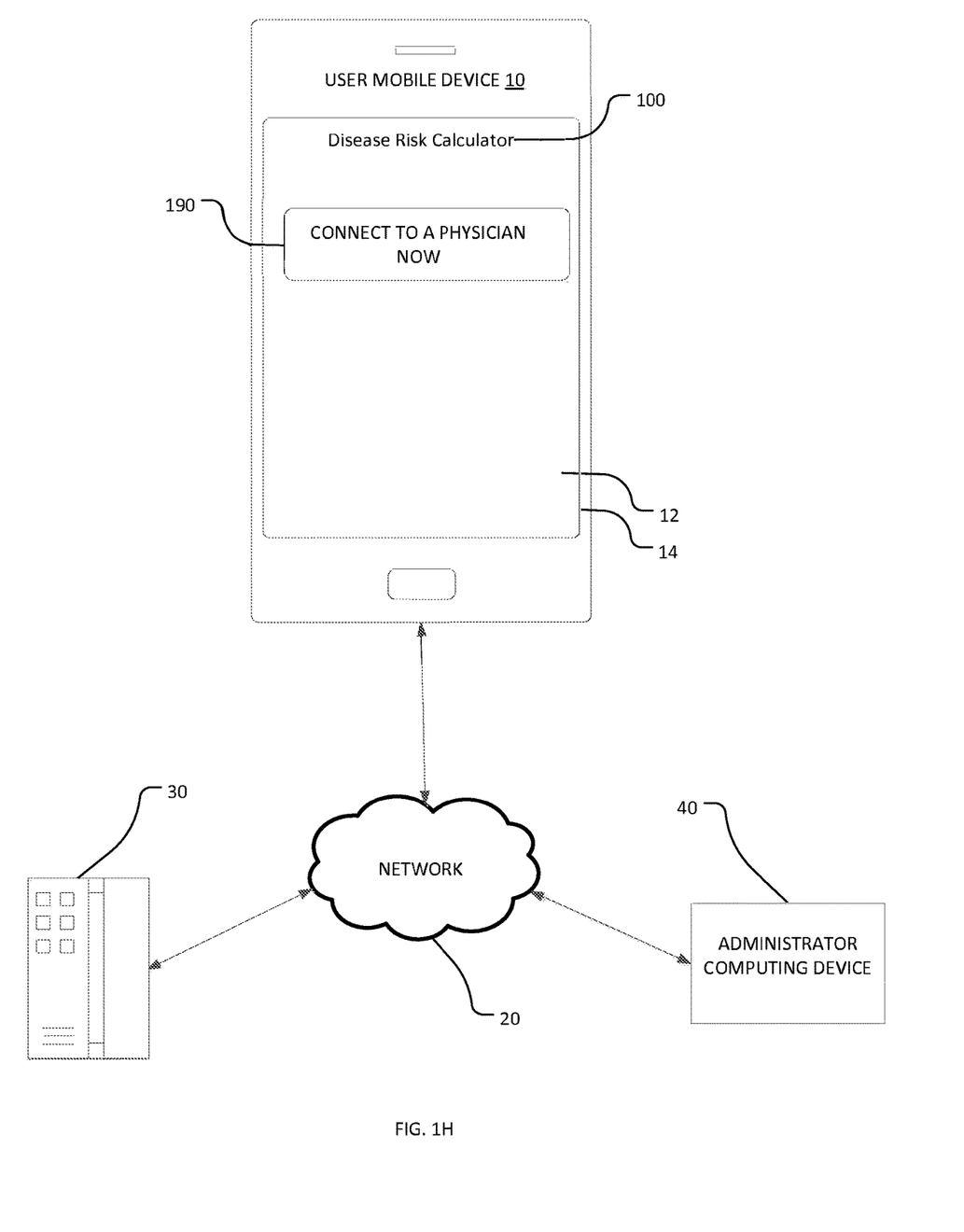

The disease risk calculation server 30 can receive the user's selection of the button 182 indicating that the user wants to consult with a physician and receive a second opinion regarding the calculated risk. The disease risk calculation server 30 can transmit to the user's mobile device 10 a link to an available physician. FIG. 1H illustrates an example of the user's mobile device 10 displaying the provided link. The GUI 12 can display the provided link represented by a button 190.

The examples of FIGS. 1A-1H are provided for example only and are not intended to be limiting. It should be appreciated that variations of the GUI 12 are contemplated and are within the scope of the disclosure.

Figure 2:
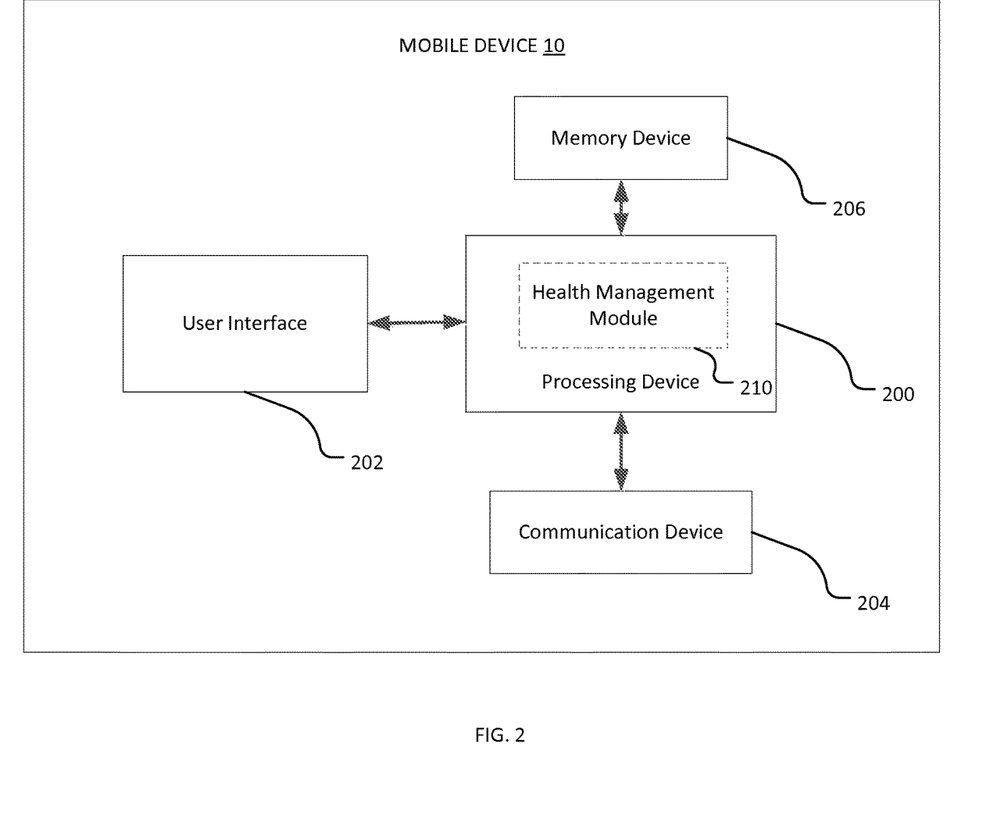
FIG. 2 is a block diagram illustrating components of the user's mobile device of FIGS. 1A-1H.

Referring now to FIG. 2, a block diagram illustrating example components of the user's mobile device 10 of FIGS. 1A-1H is depicted. In the example embodiment, the mobile device 10 includes a processing device 200, a user interface 202, a communication device 204, and a memory device 206.

The processing device 200 can include memory, e.g., read only memory (ROM) and random access memory (RAM), storing processor-executable instructions and one or more processors that execute the processor-executable instructions. In embodiments where the processing device 200 includes two or more processors, the processors can operate in a parallel or distributed manner. The processing device 200 can execute the operating system of the mobile device 10. In the illustrative embodiment, the processing device 200 also executes a disease risk calculation module 210 which is described in greater detail below.

The user interface 202 is a device that allows the patient to interact with the mobile device 10. While one user interface 202 is shown, the term "user interface" can include, but is not limited to, a touch screen, a microphone, and/or a speaker. The communication device 204 is a device that allows the mobile device 10 to communicate with another device, e.g., the disease risk calculation server 30, via the network 20. The communication device 204 can include one or more wireless transceivers for performing wireless communication. The memory device 206 is a device that stores data generated or received by the mobile device 10. The memory device 206 can include, but is not limited to, a hard disc drive, an optical disc drive, and/or a flash memory drive.

In some embodiments, the disease risk calculation module 210 is embodied as processor-executable instructions stored in the memory device 206. The processing device 200 can execute the disease risk calculation module 210. The disease risk calculation module 210 can be preloaded into the operating system of the mobile device 10, can be downloaded from the disease risk calculation server 30 or from a third party server as a downloadable app by a user of the mobile device 10, or be generated on the mobile device 10.

The disease risk calculation module 210 of the mobile device 10 provides the GUI 12 and receives user instructions via a user input to the user interface 202. The disease risk calculation module 210 further receives user answers and selections and a command to request a disease risk calculation from the disease risk calculation server 30. In response to receiving a set of diseases that the user is likely to contract from the disease risk calculation server 30, the disease risk calculation module 210 displays the set of diseases that the user is likely to contract in the GUI 12 and receives user input indicating a selection of one of the displayed diseases. In response to receiving questions related to proven risk factors of the selected disease from the disease risk calculation server 30, the disease risk calculation module 210 displays the received questions in the GUI 12 and receives user input indicating the user's responses to the displayed questions. In response to receiving a calculated risk of contracting the selected disease from the disease risk calculation server 30, the disease risk calculation module 210 displays the calculated risk in the GUI 12 and receives user input indicating the user's desire to know the meaning of the calculated risk and how the risk was calculated. The disease risk calculation module 210 receives an explanation of the meaning of the calculated risk and of how the risk was calculated from the disease risk calculation sever 30, displays the explanations in the GUI 12 and receives user input indicating the user's desire for more information and prevention tips. The disease risk calculation module 210 further receives a link to a website that provides additional information and prevention tips from the disease risk calculation server 30, displays the provided link in the GUI 12 and receives user input indicating the user's desire to consult with a physician and receive a second opinion. The disease risk calculation module 210 also receives a link to connect to an available physician from the disease risk calculation server 30 and displays the provided link in the GUI 12. In some embodiments of the present disclosure, the disease risk calculation module 210 receives a calculated risk of the user contracting the selected disease within a given time period and displays the calculated risk and time period in the GUI 12. It should be appreciated that the disease risk calculation module 210 of the mobile device 10 can be configured to perform additional functions without departing from the scope of the present disclosure.

Figure 3:
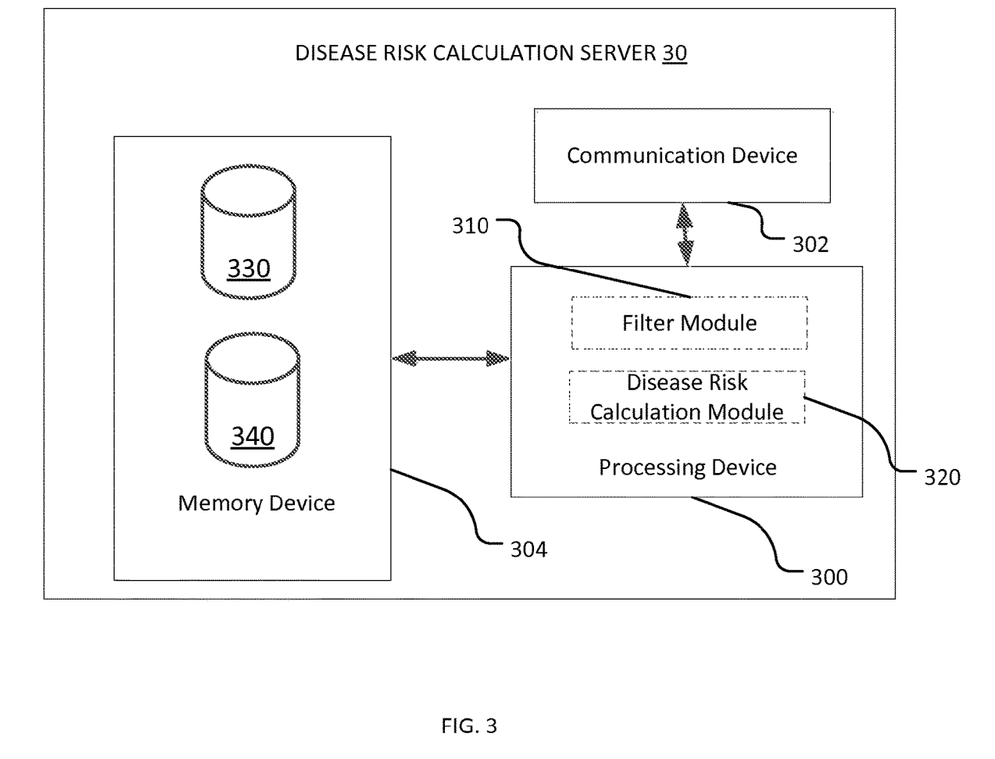
FIG. 3 is block diagram illustrating components of the disease risk calculation server of FIGS. 1A-1H.

Referring now to FIG. 3, a block diagram illustrating an exemplary disease risk calculation server 30 is depicted. In an exemplary embodiment, the disease risk calculation server 30 includes a processing device 300, a communication device 302, and a memory device 304.

The processing device 300 can include memory, e.g., read only memory (ROM) and random access memory (RAM), storing processor-executable instructions and one or more processors that execute the processor-executable instructions. In embodiments where the processing device 300 includes two or more processors, the processors can operate in a parallel or distributed manner. In the illustrative embodiment, the processing device 300 specifically executes a filter module 310 and a disease risk calculation module 320 which are described in greater detail below. The processing device 300 is specifically configured to allow filter module 310 and disease risk calculation module 320 to perform the functions as described within this disclosure.

The communication device 302 is a device that allows the disease risk calculation server 30 to communicate with another device, e.g., the user's mobile device 10, via the network 20. The communication device 302 can include one or more wireless transceivers for performing wireless communication.

The memory device 304 is a device that stores data generated or received by the disease risk calculation server 30. The memory device 304 can include, but is not limited to, a hard disc drive, an optical disc drive, and/or a flash memory drive. The memory device 304 is accessible to the processing device 300. A user database 330 and disease-risk factor database 340, or similar structures, can be stored in the memory device 304.

The user database 330 can store information related to users of the mobile based disease risk calculation system of the present disclosure. Information stored in the user database 330 can include user demographic data, answers submitted by users to provided questions, and user disease risk determinations.

The disease-risk factor database 340 can store associations between each of a plurality of diseases and proven risk factors.

The filter module 310 receives requests from the user's mobile device 10. The filter module 310 receives a request for a disease risk calculation from the user's mobile device 10. As described, the user's request can include user demographic information and answers and selections to specific questions. The filter module 310 performs a request analysis to determine a set of diseases that the user is likely to contract and provides the set of diseases to the user's mobile device 10.

The disease risk calculation module 320 receives commands from the user's mobile device 10. In response to receiving a user's selection of a disease the user selects from the set of diseases that the user is likely to contract, the disease risk calculation module 310 provides the user's mobile device 10 with at least one question related to a proven risk factor.

The disease risk calculation module 320 receives answers to the at least one provided question from the user's mobile device 10, calculates the user's risk of contracting the disease and sends the calculated risk to the user's mobile device 10. In some embodiments, the calculated risk can be either a high risk, a moderate risk, or a low risk. In some embodiments the calculated risk can be a text message sent to the user's mobile device 10. In other embodiments the calculated risk can be a graphic representation of the calculated risk. In some embodiments, the disease risk calculation module 320 can calculate and send to the user's mobile device 10 the risk that the user will contract the selected disease as a percentage. In other embodiments of the present disclosure, the disease risk calculation sever 30 can calculate and send to the user's mobile device 10 a risk that the user will contract the selected disease within a given time period.

In response to receiving a user's request for an explanation of what the calculated risk means and of how the risk was computed, the disease risk calculation module 320 sends the explanations to the user's mobile device 10. In response to receiving a user's request for additional information and prevention tips, the disease risk calculation module 320 sends a link to a website providing the requested information to the user's mobile device 10.

In response to receiving a user's request for a consultation with a physician and a second opinion, the disease risk calculation module 320 sends a link to the user's mobile device 10 that provides a means for the user to connect to an available physician.

It is appreciated that the foregoing example of the disease risk calculation server 30 is not intended to be limiting. Variations of the exemplary disease risk calculation server 30 are contemplated and within the scope of the invention. For example, the memory device 304 may store a look-up table or a hash table that relates user demographic and other information to potential diseases that the user may be at risk of contracting. In another example, the disease risk calculation server 30 can utilize artificial intelligence techniques to associate user demographic and other information with records in the disease-risk factor database 340 to increase the reliability of the set of diseases that the user may be at risk of contracting.

The disease risk calculation server 30 can also include modules that provide administrative and security functions. For example, the processing device 300 can execute a registration module to provide users with an interface for entering registration information such as name, address, date of birth, and email address.

Figure 4:
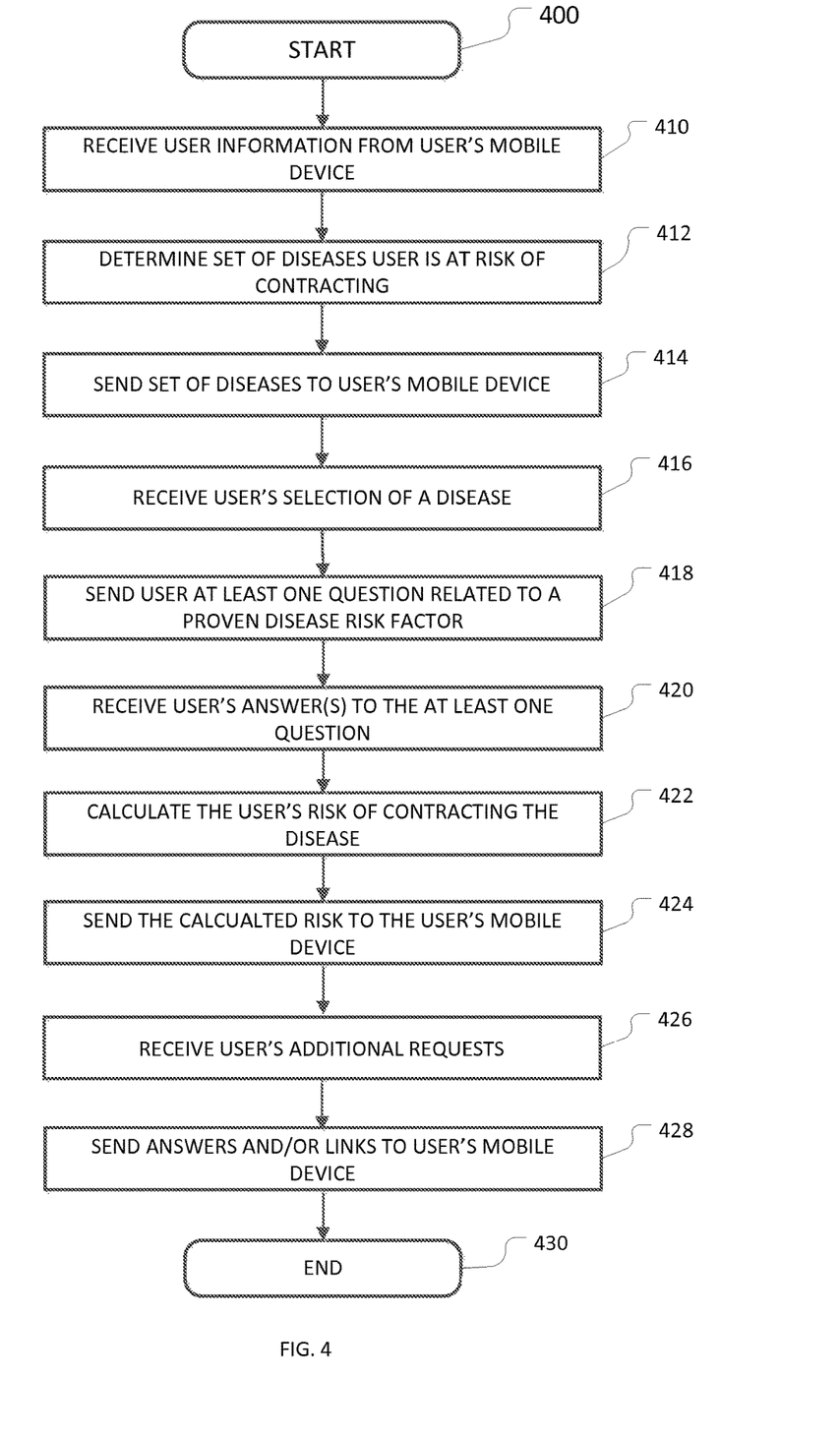
FIG. 4 is a flow chart illustrating an example method for providing an automated disease risk calculation in accordance with some embodiments of the present disclosure.

Referring now to FIG. 4, an example method 400 for providing a mobile based disease risk calculation is illustrated. In some embodiments of the present disclosure, the disease risk calculation server 30 (FIG. 3) executes the method 400. The flowchart and block diagrams illustrate the architecture, functionality, and operation of possible implementations of systems, methods, and computer program products according to various embodiments of the present disclosure. In this regard, each block in the flowchart or block diagram may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

At operation 410, the filter module 310 receives the user information from the user's mobile device 10. As discussed above, the GUI 12 of the user's mobile device 10 allows the user to submit demographic and other information used by the filter module 310 to screen the number of disease that the user is likely to contract. At operation 412, the filter module 310 determines a set of diseases that the user is likely to contract based upon the received user information. At operation 414, the filter module 310 provides the set of diseases to the user's mobile device 10. In some embodiments of the present disclosure, the filter module 310 can provide a list of additional, selectable diseases to the user's mobile device 10.

At operation 416, the disease risk calculation module 320 receives a user selection indicating the user's selection of a disease that the user desires to know his risk of contracting. At operation 418, the disease risk calculation module 320 sends at least one question related to a known disease risk factor to the user's mobile device 10. At operation 420, the disease risk calculation module 320 receives user answers to the at least one question from the user's mobile device 10. At operation 422, the disease risk calculation module 320 calculates the user's risk of contracting the selected disease based upon the user's answers. At operation 424, the disease risk calculation module 320 sends the calculated disease risk to the user's mobile device 10. At operation 426, the disease risk calculation module 320 receives additional requests from the user's mobile device 10 and at operation 428, the disease risk calculation module 320 sends the user's mobile device answers and/or links to the additional requests.

The method 400 of FIG. 4 is provided for example and is not intended to be limiting. It should be appreciated that the method 400 can include additional operations and some operations may be varied or eliminated without departing from the scope of the disclosure. For example, the disease risk calculation module 320 can calculate and send to the user's mobile device 10 a calculated risk that the user will contract the selected disease within a given time period.

In other embodiments, the present disclosure utilizes blockchain technology to govern disputes, govern electronic payments, and establish communication directly between parties without third-party intermediaries. Blockchains are decentralized, peer-to-peer networked databases that can store and authenticate a ledger of assets and asset transactions. Blockchain technology allows transactions to occur without a third-party intermediary. Blockchain technology uses smart contracts to resolve disputes. Smart contracts are computer programs designed to act as self-executing contracts that implement aspects of a transaction where the terms of the agreement between buyer and seller are directly written into lines of software code. The code and the agreements exist across a distributed, decentralized blockchain network, specifically using a smart contracts concept, which allows for instantaneous payment.

The present disclosure allows for transactions to take place across a blockchain database. So, for example, when the disease risk calculation module 320 sends the calculated disease risk to the user's mobile device 10, arrangements can be made for the user to pay for the services rendered by the disease risk calculation server 30, a physician or physicians that provide a second opinion, or any other entity, electronic payment can be arranged using the afore-mentioned blockchain technology. Thus, electronic payment received from the user device can be processed by the processor at the disease risk calculation server 30 or another module disclosed herein, after the user device receives or confirms receipt of the calculated risk, where the electronic payment is governed by blockchain technology, including for example smart contracts.

Further, the present disclosure allows for all second opinions to be stored in a blockchain database. In one embodiment, processing device 300 automatically selects one or more physicians from a pool of physicians to render a second opinion. This selection can be based on physician criteria and expertise. In another embodiment, artificial intelligence ("AI") algorithms are used to help physicians provide more accurate second opinions and in a more timely fashion.

The above description of illustrated examples of the present invention, including what is described in the Abstract, are not intended to be exhaustive or to be limitation to the precise forms disclosed. While specific embodiments of, and examples for, the invention are described herein for illustrative purposes, various equivalent modifications are possible without departing from the broader spirit and scope of the present invention.

I claim:

1. A computer-implemented method comprising the steps of:
   receiving, at a processing device of a disease risk calculation server, a request from a user mobile device, the request being indicative of the user's request for a disease risk calculation and including an answer to at least one screening question;
   determining, at the processing device, a set of diseases the user is likely to contract based upon the answer to the at least one screening question;
   providing, from the processing device, the determined set of diseases the user is likely to contract to the user mobile device;
   receiving, at the processing device, a user selection of a disease from the set of diseases that user is likely to contract;
   providing, from the processing device, at least one question related to at least one proven risk factor of the user selected disease to the user mobile device;
   receiving, at the processing device, a user answer to the at least one question, the user answer containing at least the at least one proven risk factor;
   calculating, at the processing device, a risk that the user will contract the selected disease, the calculation based at least on a number of proven risk factors received by the processing device and a degree of association between the risk factor and the selected disease;
   providing, from the processing device, the calculated risk to the mobile device; and
   receiving and processing electronic payment from the user device after receipt by the user mobile device of the calculated risk, the electronic payment being governed by blockchain technology.

2. The computer-implemented method of claim 1, wherein the at least one screening question includes a question related to the user's age.

3. The computer-implemented method of claim 1, wherein the at least one screening question includes a question related to the user's gender.

4. The computer-implemented method of claim 1, wherein the at least one screening question includes a question related to the user's ethnicity.

5. The computer-implemented method of claim 1, wherein the at least one screening question includes a question related to the user's genetic predisposition to a disease.

6. The computer-implemented method of claim 1, wherein calculating, at the processing device, a risk that the user will contract the selected disease based on the user answer to the at least one question comprises assigning equal weights to user answers to the at least one question.

7. The computer-implemented method of claim 1, wherein calculating, at the processing device, a risk that the user will contract the selected disease based on the user answer to the at least one question comprises assigning weighted values to user answers to the at least one question.

8. The computer-implemented method of claim 1, wherein calculating, at the processing device, a risk that the user will contract the selected disease based on the user answer to the at least one question comprises assigning a greater weight to the user answer to the at least one question indicating a genetic predisposition to the selected disease.

9. The computer-implemented method of claim 1, wherein calculating, at the processing device, a risk that the user will contract the selected disease based on the user answer to the at least one question comprises calculating a risk that the user will contract the selected disease within a given time period.

10. The computer-implemented method of claim 1, wherein providing, from the processing device, the calculated risk to the mobile device comprises providing the calculated risk as one of a group consisting of high, moderate and low.

11. The computer-implemented method of claim 1, wherein providing, from the processing device, the calculated risk to the mobile device comprises providing the calculated risk as a percentage.

12. A disease risk calculation server having a processing device, the disease risk calculation server comprising:
   a filter module configured to:
   (a) receive a request from a user mobile device, the request being indicative of the user's request for a disease risk calculation and including an answer to at least one screening question;
   (b) determine a set of diseases the user is likely to contract based upon the answer to the at least one screening question; and
   (c) provide the determined set of diseases the user is likely to contract to the user mobile device; and
   a disease risk calculation module configured to:
   (a) receive a user selection of a disease from the set of diseases that the user is likely to contract;
   (b) provide at least one question related to a at least one proven risk factor of the user selected disease to the user mobile device;
   (c) receive a user answer to the at least one question, the user answer containing at least the at least one proven risk factor;
   (d) calculate a risk that the user will contract the selected disease, the calculation based at least on a number of proven risk factors received by the processing device and a degree of association between the risk factor and the selected disease;
   (e) provide the calculated risk to the mobile device; and
   (f) receive and process electronic payment from the user device after receipt by the user mobile device of the calculated risk, the electronic payment being governed by blockchain technology.

13. The disease risk calculation server of claim 12, wherein the at least one screening question includes a question related to the user's age.

14. The disease risk calculation server of claim 12, wherein the at least one screening question includes a question related to the user's gender.

15. The disease risk calculation server of claim 12, wherein the at least one screening question includes a question related to the user's ethnicity.

16. The disease risk calculation server of claim 12, wherein the at least one screening question includes a question related to the user's genetic predisposition to a disease.

17. The disease risk calculation server of claim 12, wherein the disease risk calculation module is configured to calculate the risk that the user will contract the selected disease by assigning equal weights to user answers to the at least one question.

18. The disease risk calculation server of claim 12, wherein the disease risk calculation module is configured to calculate the risk that the user will contract the selected disease by assigning weighted values to user answers to the at least one question.

19. The disease risk calculation server of claim 12, wherein the disease risk calculation module is configured to calculate the risk that the user will contract the selected disease by assigning a greater weight to the user answer to the at least one question indicating a genetic predisposition to the selected disease.

20. The disease risk calculation server of claim 12, wherein the disease risk calculation module is configured to calculate the risk that the user will contract the selected disease by calculating a risk that the user will contract the selected disease within a given time period.

* * * * *